(12) United States Patent
Marie-Catherine

(10) Patent No.: US 8,267,093 B2
(45) Date of Patent: Sep. 18, 2012

(54) DEVICE FOR ARTICULATING AN ORTHODONTIC SYSTEM CAPABLE OF CAUSING THE MOVEMENT OF A MANDIBLE IN RELATION TO A MAXILLA

(75) Inventor: Franck Marie-Catherine, Royat (FR)

(73) Assignee: Orthogem, Clermont Ferrand (FR)

( * ) Notice: Subject to any disclaimer, the term of this patent is extended or adjusted under 35 U.S.C. 154(b) by 127 days.

(21) Appl. No.: 12/819,735

(22) Filed: Jun. 21, 2010

(65) Prior Publication Data

US 2011/0311936 A1    Dec. 22, 2011

(51) Int. Cl.
*A61F 5/56* (2006.01)
*A61C 5/14* (2006.01)
*A61C 3/00* (2006.01)

(52) U.S. Cl. ........ 128/848; 128/859; 128/860; 128/861; 128/862; 433/6

(58) Field of Classification Search .................. 128/846, 128/848, 856–863, 898; 433/19, 24, 6, 18, 433/20, 21, 7, 34, 37, 41–44, 140; 602/902
See application file for complete search history.

(56) References Cited

U.S. PATENT DOCUMENTS 5,829,975 A * 11/1998 Gold ............................... 433/19

* cited by examiner

*Primary Examiner* — Patricia Bianco
*Assistant Examiner* — Nihir Patel
(74) *Attorney, Agent, or Firm* — Heslin Rothenberg Farley & Mesiti P.C.

(57) ABSTRACT

An orthodontic assembly articulation device for causing a mandible to move relative to a maxilla includes a lower splint fitted with a lower reinforcement and an upper splint fitted with an upper reinforcement. The reinforcements are connected by a system of rods mounted with sliding capability. A ball joint couples each system of rods with a part of the reinforcements. The ball joint is interdependent with an extension oriented perpendicularly and screwed into a support element interdependent with a corresponding part of the reinforcements. The ball joint engages with the hemispherical cage of an end piece secured to each system of rods. The cage is in communication with an opening of the end piece to allow articulation of the system of rods of about 90° in a vertical plane and about 360° in a horizontal plane, while preventing any swinging of the end piece.

8 Claims, 4 Drawing Sheets

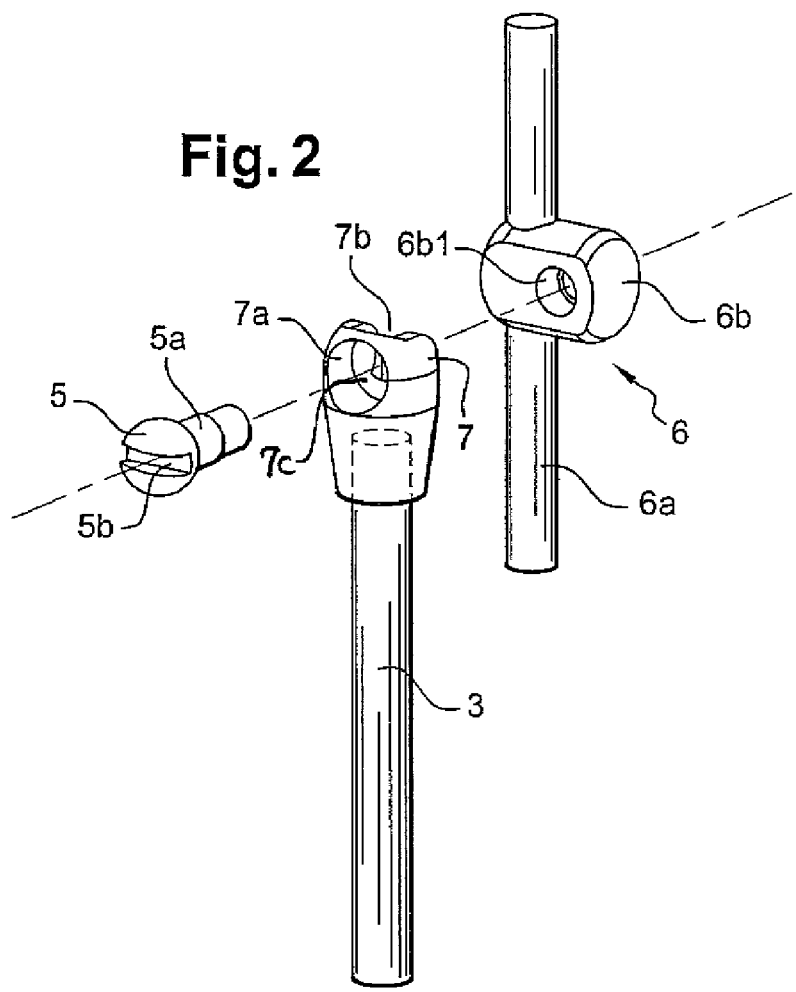
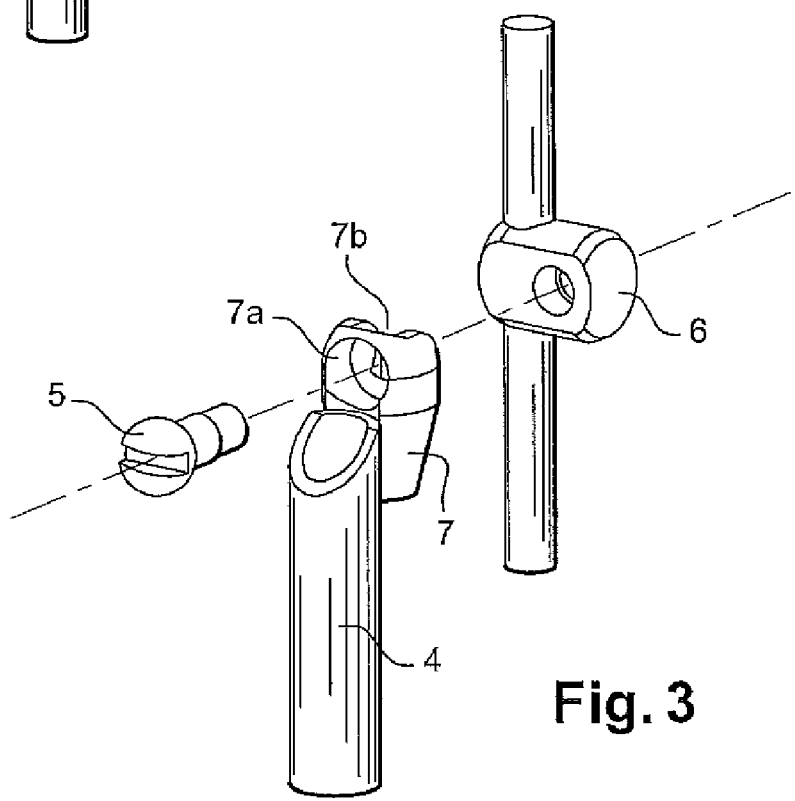

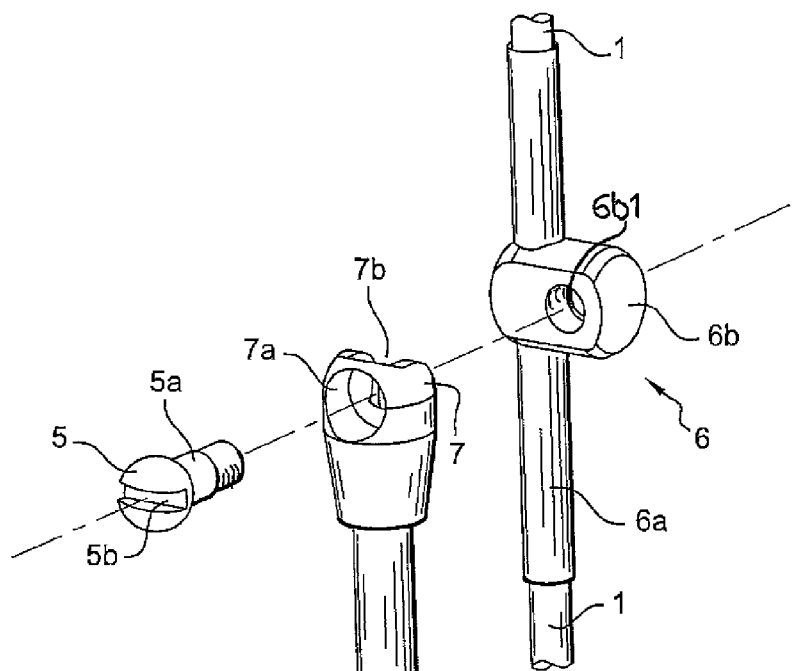
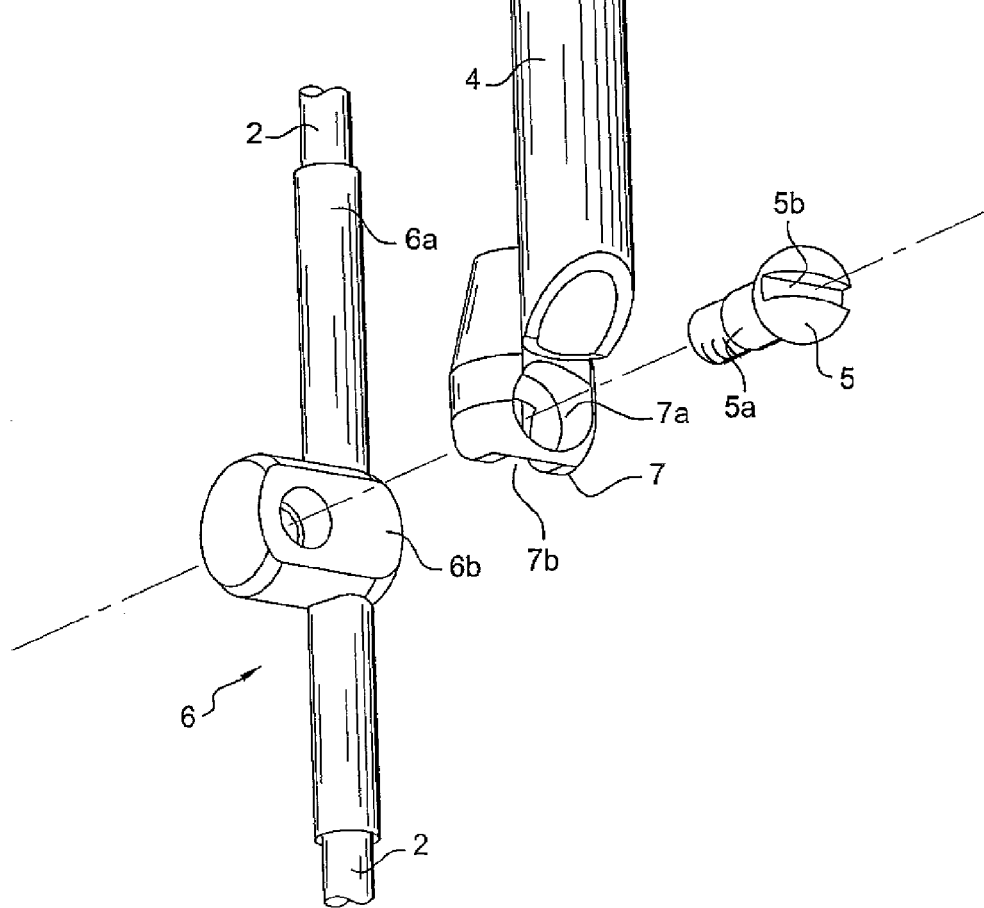
Fig. 6

US 8,267,093 B2

DEVICE FOR ARTICULATING AN ORTHODONTIC SYSTEM CAPABLE OF CAUSING THE MOVEMENT OF A MANDIBLE IN RELATION TO A MAXILLA

BACKGROUND ART

The invention relates to the technical field of mandibular advancement orthoses. Different solutions have been proposed for causing the mandible to move relative to the maxilla.

The required aim is to move the mandible forward relative to its original position by a very small distance of the order of a few millimeters, initially, in order, in particular, to stimulate growth. This mandibular propulsion may be used to increase respiratory flow, in order to sort out sleep apnoea syndrome problems.

The invention relates more particularly to an orthodontic assembly of the type perfectly understood by those skilled in the art and known as a "Herbst orthosis" or "Herbst rods".

Essentially, this type of orthosis has splints engaging with the row of top teeth and the row of bottom teeth, respectively. These splints are generally made out of a rigid material, for example thermo-formed acrylic resin, and are connected to each other by a system of rods mounted with sliding capability. To be more precise, two metal rods are arranged, respectively, on each side of a reinforcement made interdependent with a part of the upper splint and lower splint. The two rods are connected with articulation capability on the reinforcement, substantially at primary molar level in respect of the upper splint and substantially at canine level in respect of the lower splint. The rods, on the corresponding reinforcement parts, as previously indicated, are articulated by means of an axis arranged in a substantially horizontal plane, such that the articulation movement of the rods is restricted in a vertical plane.

This restricted movement of the mandible relative to the maxilla, in a postero-anterior direction, is not satisfactory. It has proved important, for patients fitted with this type of orthodontic assembly, to be able also to have a high level of freedom of lateral movement of the mandible relative to the maxilla. It has also been noted that this type of horizontal axis articulation is cumbersome and makes it tricky to engage the rods of the upper and lower splints.

Systems for the articulation of an orthopaedic assembly are also known wherein the rods are coupled with the upper and lower splints, by means of a ball joint. The teaching in U.S. Pat. No. 5,620,321 may, for example, be cited. However, the solution described in this patent is not totally satisfactory given that it is not possible to obtain laterality movements.

The aim of the invention has been to overcome these drawbacks in a straightforward, safe, effective and rational manner.

The problem the invention sets out to resolve is how to confer total freedom of articulation of the rods both in an antero-posterior plane and in a lateral plane, and to do so while occupying less space.

BRIEF SUMMARY OF THE INVENTION

To resolve said problem, a device has been designed and perfected for the articulation of an orthodontic assembly capable of causing a mandible to move relative to a maxilla, each being fitted with a lower reinforcement and an upper reinforcement connected by a system of rods mounted with sliding capability. The device includes, for each rod, ball joint type means for coupling with a part of the corresponding reinforcements. The ball joint is interdependent with an axis orientated perpendicularly and screwed into a support element interdependent with a part of the corresponding reinforcement, said ball joint engaging with a hemispherical cage of an end piece secured to each rod, said cage being in communication with an opening of the end piece, established so as to allow an articulation of the rods of about 90° in a vertical plane and about 360° in a horizontal plane, while preventing any swinging of the end piece.

The result of these features is perfect control of the mandibular propulsion (antero-posterior movement) and laterality movements, preventing any effect of swinging of the coupling end piece and, consequently, of the rods.

To resolve the problem posed of preventing any swinging effect, the end piece opening, in communication with the hemispherical cage, is defined by two parallel vertical wings that prevent any swinging, i.e. any oscillatory motion.

For coupling the end piece and the articulation ball joint, two embodiments are conceivable.

In a first embodiment, the ball joint axis is inserted into a through hole in the hemispherical cage, so that it can be screwed into the support element.

In a second embodiment, the ball joint is inserted into the hemispherical cage from a notch in communication with said cage, in a 90° position from the rod, which is then folded back angularly into the coupling position.

In one embodiment and on the mandible side, the end piece has a counterbore so it can be secured coaxially to the rod.

In one embodiment and on the maxilla side, the end piece is secured by being superposed onto one of the ends of the rod.

To resolve the problem posed of improving the articulation of the rods, while complying with a small space requirement, the support element is offset laterally relative to the corresponding reinforcement part. The support element has a sleeve for coupling with the corresponding reinforcement part, said sleeve having an offset bush in which the ball joint axis is secured.

BRIEF DESCRIPTION OF THE DRAWING FIGURES

The invention is disclosed hereinafter in further detail with the help of the figures in the appended drawings wherein:

FIG. 2 is a perspective view prior to assembly of the end of one of the rods on the support element considered on the mandible side;

FIG. 3 is a perspective view prior to assembly of the end of the rod on the support element considered on the maxilla side;

FIG. 6 is a perspective view after coupling of the rods and prior to assembly on the corresponding support element;

DETAILED DESCRIPTION

Figure 1:
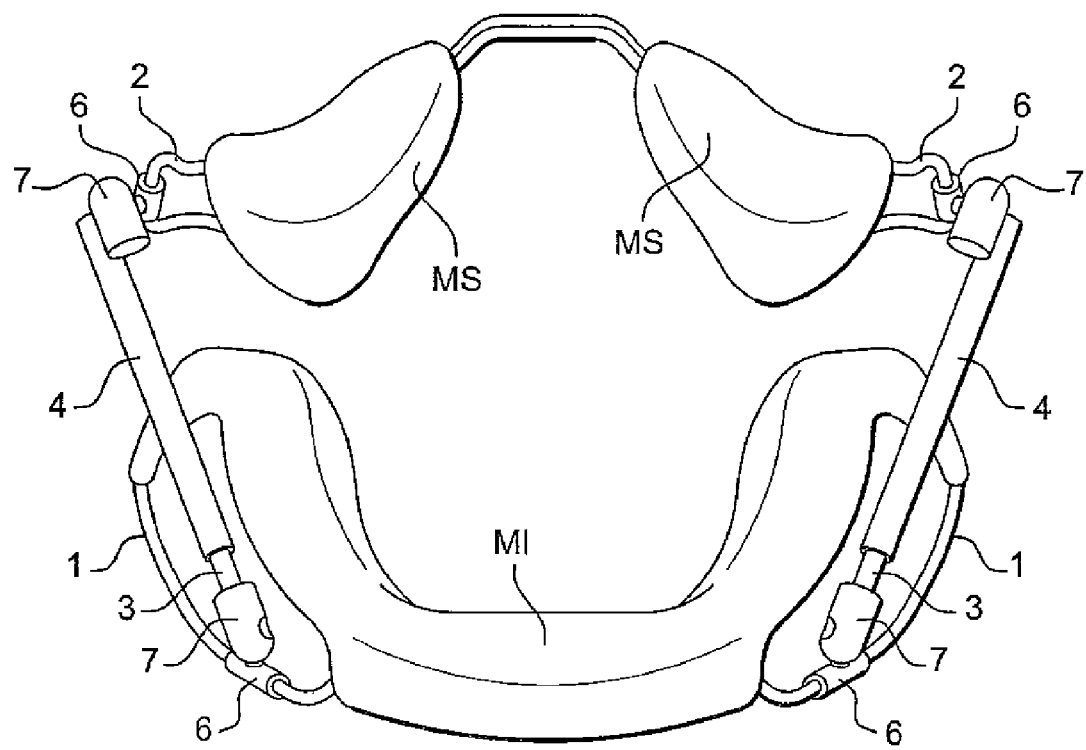
FIG. 1 is a diagrammatic perspective view showing an orthodontic assembly whereof the upper and lower splints are connected by a system of rods mounted with articulation capability, according to the characteristics of the inventive device.

FIG. 1 has been used to show, as an informative but in no way restrictive example, an orthodontic assembly for moving the mandible relative to the maxilla. In a way perfectly understood by those skilled in the art, this assembly may be constituted by an upper splint (MS) engaging with a part of the maxilla dentition and a lower splint (MI) engaging with all or part of the mandible dentition.

As already indicated, each splint (MS) and (MI) is made by thermo-forming or of resin with the "pepper and salt" technique by adding a track on the mandibular occlusal part and on the maxilla occlusal part. Additionally, each of the splints (MS) and (MI) has reinforcements (1) and (2) for coupling, with articulation capability, a system of rods (3) and (4) mounted with capability of linear sliding guided in translatory motion. This assembly is implemented symmetrically on either side of the longitudinal axis of each of the splints.

The invention also applies in the event of the reinforcements (1) and (2) constituting an arch connecting brackets of a dental appliance provided on the mandibular arch and the maxillary arch.

In the example shown, each of the rods (3) is articulated on a part of the reinforcement (1) of the lower splint relative to the mandible, while each of the rods (4) is articulated on a part of the reinforcement (2) relative to the upper splint of the maxilla.

According to one basic inventive feature, the articulation device includes, for each rod (3) and (4), coupling means of the ball joint type, capable of allowing, in a horizontal plane, an articulation of about 360° of the corresponding rod and, in a vertical plane, an articulation of about 90° at least of the corresponding rod. Importantly, the ball joint (5) is interdependent with an axis or extension (5a) oriented perpendicular to a support element (6) interdependent with a part of the corresponding reinforcement (1) or (2).

The support (6) is interdependent with the reinforcement (1) or (2) by any known and appropriate means, as will be indicated in the remainder of the description.

For each of the rods (3) and (4), the coupling means are constituted by an end piece (7) that has a hemispherical cage (7a) capable of accommodating the ball joint (5). Importantly, this hemispherical cage (7a) is in communication with a through opening (7b) on one side of the end piece formed perpendicular to its longitudinal axis and in a plane parallel to the one accommodating the axis (5a) of the sphere (5). The opening (7b) defines two parallel vertical wings (7b1)-(7b2) that prevent any swinging of the end piece (7) and, consequently, of the rods, after coupling with the ball joint (5). Swinging is taken to mean any oscillatory motion in a horizontal plane.

Figure 4:
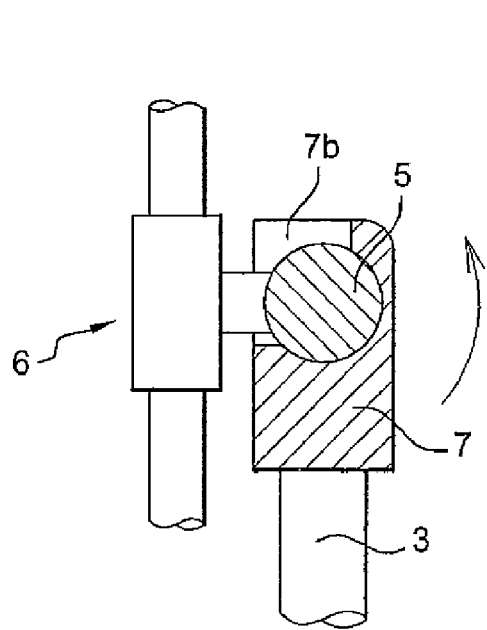
FIG. 4 is a partial longitudinal cross-section view showing the principle of the articulation of the rods relative to a support element in an antero-posterior plane of about 90°.
Figure 5:
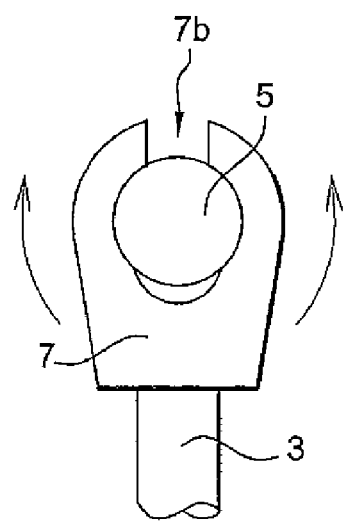
FIG. 5 is a plan view corresponding to FIG. 4 showing the principle of articulation in a lateral plane (360°)

After the end piece (7) has been coupled to the sphere (5) made interdependent with the support element (6), the opening (7b) allows a vertical movement of the rod (3) or (4) of about 90°. It is therefore clear that this ball joint type articulation, with the sphere (5) in combination with the opening (7b) of the end piece (7), allows, in a horizontal plane, a movement of about 360° (FIG. 5) and, in a vertical plane, a movement of about 90° (FIG. 4), while preventing a swinging effect of said end piece. Perfect control is thus achieved of mandibular propulsion and laterality movements.

Depending on the intended use, different solutions are conceivable for coupling the end piece (7) relative to the ball joint (5).

In one embodiment shown in FIGS. 2, 3 and 6 in particular, the end piece (7) has a hole (7c) leading into the hemispherical cage (7a) and into the opening (7b). In this event, the ball joint (5) is engaged from its axis (5a) in the hole (7c) and in the opening (7b) in order to be screwed into a tapped hole (6b1) of the support (6).

Figure 7:
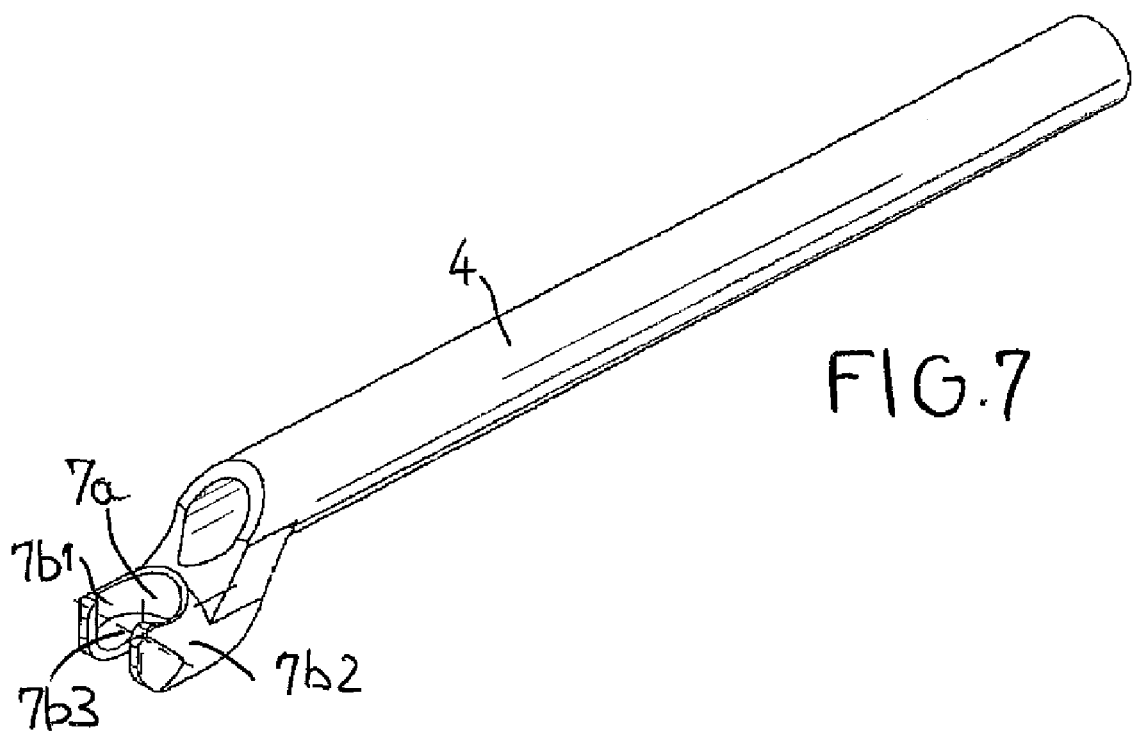
FIG. 7 is a perspective view of another embodiment of the end piece, particularly with a view to its snap-on coupling relative to the ball joint.

In the embodiment shown in FIG. 7, the opening (7b) defines, in combination with the hemispherical cage (7a), a notch (7b3). In this event, the ball joint (5) is pre-screwed by its axis (5a) into the support (6b). The end piece (7) with the corresponding rod, is positioned at 90° in order to be engaged on the ball joint (5) and then folded back angularly into the coupling position. Put another way, the end piece (7) is coupled on the ball joint (5) from the notch (7b3) in a 90° position from the corresponding rod.

The part of the support element (6) accommodating the ball joint (5) is offset laterally relative to the corresponding reinforcement part (1) or (2). For example, the support element (6) has a coupling sleeve (6a) secured to the reinforcements (1) and (2), which sleeve (6a) has a bushing (6b) in which the extension (5a) of the ball joint (5) is secured.

It will be remembered, in a known way, that the zone of articulation of the rods (3) and (4), relative to the corresponding parts of the reinforcements (1) and (2), is established so as to equate in general terms to primary molar level in respect of the maxilla splint and canine level in respect of the mandible splint. The support element (6) is therefore positioned and secured as a consequence to the corresponding reinforcement parts (1) and (2).

As shown, the axis (5a) of the ball joint (5) is secured to the support element (6) with disassembly capability by being screwed into the tapped hole (6b1) of the support (6). Apart from this resulting disassembly capability, the coupling of each of the rods (3) and (4) with the bushing (6b) on the support element (6), in combination with the ball joint (5), is particularly straightforward and fast. Indeed, the end piece (7) has only to be positioned on the corresponding part of the support (6) and the extension (5a) of the sphere (5) inserted into the hemispherical cage (7a) of the end piece (7), so that it can be screwed into the tapped hole (6b) of the support element (6).

It will be remembered that it is also possible to secure the ball joint (5) in the support (6), and then to engage at 90° the end piece (7) from the forward opening notch (7b3).

In an embodiment shown in FIG. 2, the coupling end piece (7) is arranged coaxially to the rod (3). For example, the end piece (7) has a counterbore (7c) in which the end of the rod (3) is secured, by any known and appropriate means. This solution is, for example, used for rods coupled with articulation capability on the mandible side.

In the embodiment shown in FIG. 3, the coupling end piece (7) is secured being superposed on the end of the rod (4). This embodiment is, for example, used for the rods coupled with articulation capability on the maxilla side.

Quite clearly, the end piece (7) and the rods (3) and (4) may be constituted by a single element, cast in one piece.

In a conventional way perfectly understood by those skilled in the art, the rod (3), for example, is mounted with guided linear sliding capability inside the rod (4). Put another way, for example, the rod (3) is constituted by a full cylindrical body, while the rod (4) is constituted by a tube. Reference may be made to FIG. 6 which shows the coupling of the two rods prior to assembly on their respective support elements (6), in the aforementioned conditions.

It should be noted that, to facilitate the assembly and disassembly of the articulation device, the ball joint (5) has an impression or groove (5b) capable of engaging with a handling component such as a screwdriver, for example.

After coupling, the tube constituting the rod (4) is stopped against the end piece (7) of the cylindrical body or shank, constituting the rod (3). Rings may be added to the cylindrical rod to control clearance.

Figure 8:
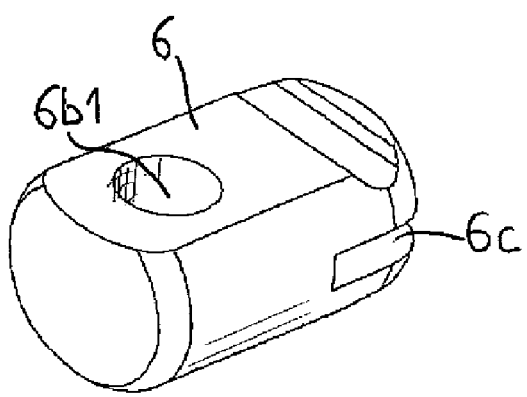
FIG. 8 is a perspective view of an embodiment of the support element with a view to securing it, particularly by insetting, to the reinforcements constituted by a dental arch.

The support element (6) may have arrangements (6*c*) (FIG. 8) so that it can be inset directly onto the reinforcements (1) and (2) in the event particularly of said reinforcements constituting a dental arch fitted, in a known way, with brackets.

The advantages are clear from the description, and in particular the following are stressed and recalled:

- the reduction in required space and resulting comfort;
- the great freedom of lateral movement;
- the ease with which the articulation device can be assembled and disassembled relative to the reinforcements or the like, it being stressed that it is possible for the ball joint to be secured in the conditions indicated, in the material constituting the splints, in other orthodontic arrangements, to multi-fastening appliances, etc.
- the design of the articulation, particularly as regards the end piece (7), is established to protect against any projection of the rod, in order to prevent any risk of injury;
- the oscillation on both axes at a point 0, without swinging and without lateral limitation, with a ball joint axis arranged vertically.

The invention claimed is:

1. Orthodontic assembly articulation device for causing a mandible to move relative to a maxilla, the device including a lower splint fitted with a lower reinforcement and an upper splint fitted with an upper reinforcement, said upper reinforcement and said lower reinforcement being connected by a system of rods mounted with sliding capability, a ball joint for coupling each system of rods with a part of at least one of the lower and upper reinforcements, wherein the ball joint includes a ball having an extension oriented perpendicularly and screwed into a support element affixed to a corresponding part of the lower reinforcement or upper reinforcement, and an end piece secured to each system of rods, the end piece having an open ended outwardly facing hemispherical cage engaging the ball and a through opening bounded by a pair of parallel vertical wings opposite and in communication with the hemispherical cage and receiving the extension to allow an articulation of the system of rods of about 90° in a vertical plane and about 360° in a horizontal plane, while the wings interface with the extension and prevent any swinging of the end piece.

2. Device as claimed in claim 1, wherein the ball of the ball joint has a groove for receiving a tool opposite the extension.

3. Device as claimed in claim 1, wherein the extension of the ball joint is inserted into a hole leading into the hemispherical cage, so that the extension can be screwed into the support element.

4. Device as claimed in claim 1, wherein the ball joint is inserted into the hemispherical cage from a notch in communication with said cage, in a 90° position from the system of rods, and is then folded back angularly into a coupling position.

5. Device as claimed in claim 1, wherein the end piece has a counterbore securing the end piece coaxially to the system of rods.

6. Device as claimed in claim 1, wherein the end piece is secured by being superposed on one end of the system of rods.

7. Device as claimed in claim 1, wherein the support element is offset laterally relative to the corresponding part of the lower reinforcement or upper reinforcement.

8. Device as claimed in claim 1, wherein the support element has a coupling sleeve secured to the corresponding part of the lower reinforcement or upper reinforcement, said sleeve having an offset bushing in which the extension of the ball joint is secured.

* * * * *